United States Patent [19]

Kiekhafer et al.

[11] Patent Number: 4,934,049
[45] Date of Patent: Jun. 19, 1990

[54] METHOD FOR FABRICATION OF A MEDICAL ELECTRODE

[75] Inventors: Thomas Kiekhafer, Coon Rapids; Edward DiDomenico, Anoka; Kenneth Keeney, Forest Lake; Bruce Johnson, Loretto, all of Minn.

[73] Assignee: Medtronic, Inc., Minneapolis, Minn.

[21] Appl. No.: 376,731

[22] Filed: Jul. 7, 1989

[51] Int. Cl.$^5$ .............................................. H01R 43/16
[52] U.S. Cl. ........................................ 29/883; 29/605; 29/825; 128/419 P; 128/784; 128/786
[58] Field of Search ..................... 29/883, 825, 605; 219/121.4, 121.41; 174/69; 128/419 P, 784, 786

[56] References Cited

U.S. PATENT DOCUMENTS

| | | | |
|---|---|---|---|
| 3,416,534 | 12/1968 | Quinn | 128/419 P |
| 4,161,952 | 7/1979 | Kinney et al. | 128/786 |
| 4,381,014 | 4/1983 | Sandstrom et al. | |
| 4,437,474 | 3/1984 | Peers-Trevarton | 29/876 X |
| 4,458,695 | 7/1984 | Peers-Trevarton | 128/419 P X |
| 4,592,372 | 6/1986 | Beranek | 128/786 |
| 4,817,634 | 4/1989 | Holleman et al. | 128/784 |

OTHER PUBLICATIONS

Brochure entitled, "Plasma Surface Chemistry", published by Branson/IPC, a SmithKline Company.

Primary Examiner—Carl J. Arbes
Attorney, Agent, or Firm—Reed Duthler; Joseph F. Breimayer

[57] ABSTRACT

A process for producing a medical electrode. A coil of conductive metal is slid over a tubular insulative substrate. The spaces between individual turns of the coil are backfilled with an insulative plastic. The backfilled plastic is thereafter etched away from and off of the exterior of the metal coil by means of a gas plasma.

1 Claim, 1 Drawing Sheet

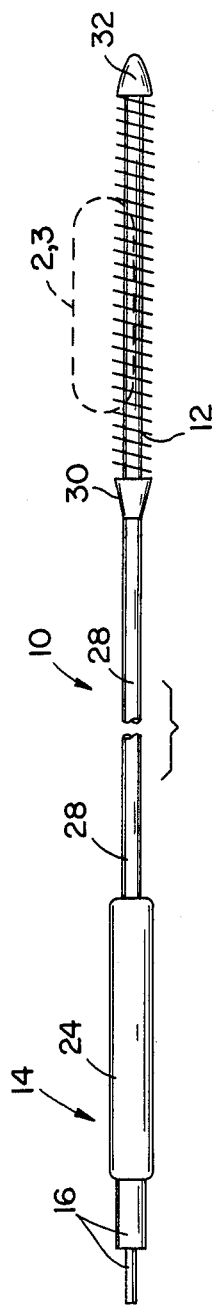
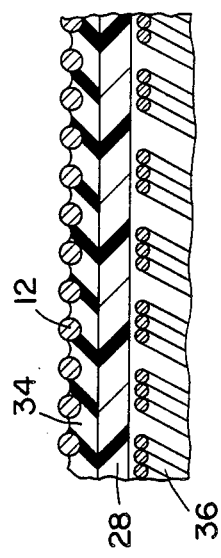
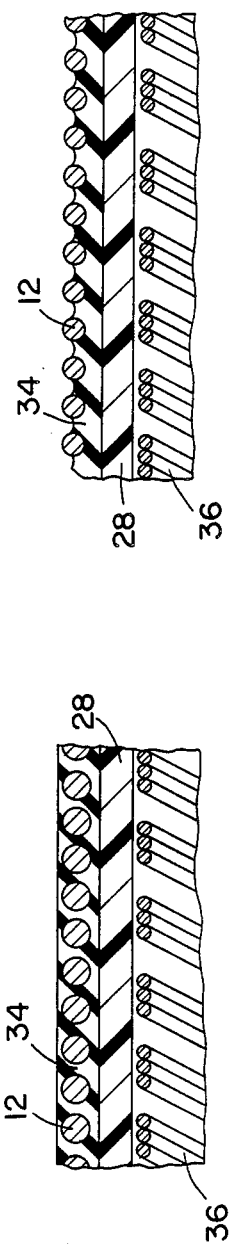

METHOD FOR FABRICATION OF A MEDICAL ELECTRODE

BACKGROUND OF THE INVENTION

This invention relates to medical electrical stimulation electrodes in general, and to defibrillation electrodes in particular.

In the past years, there has been substantial activity toward development of a practical, implantable defibrillator. Most proposals involve the use of large surface area implantable electrodes, either to be mounted within the heart, on the exterior of the heart, or subcutaneously. One common approach of providing a large surface area electrode is to employ an elongated exposed coil of biocompatible metal. In the context of an endocardial lead, this is disclosed in U.S. Pat. No. 4,161,952 issued to Kinney et al. In the context of an epicardial electrode, this is disclosed in the context of U.S. Pat. No. 4,187,634 issued to Holleman et al.

In an endocardial lead, an elongated coil serving as the electrode, can be mounted around the exterior of an insulative lead body. It is believed desirable in this context to stabilize the electrode coil with respect to the lead body, both to provide mechanical integrity and to prevent fibrous ingrowth around the individual coils of the electrode. In the above-cited Kinney et al patent, this is accomplished by molding the exposed electrode coil into the surface of the lead body. The entire exterior surface of the electrode may then be machined to provide a smooth surface of alternating conductive areas from the electrode coil and insulative areas from the lead body.

SUMMARY OF THE INVENTION

The present invention is directed towards an improved method of producing an elongated electrode, typically for use on an endocardial defibrillation lead. The electrode coil is slipped around the insulative lead body, and placed inside a tight fitting tubular member which defines an injection molding space between the tubular member, the coils of the electrode, and the lead body. Silicone rubber or other insulative material is then injected into the spaces between the electrode coils, the outer tube and the lead body.

Typically, the inventors have used heat shrink tubing to form the outer tubular member, shrunk down tightly around the external diameter of the coil. Nonetheless, it has been determined that after the step of injection of silicone rubber, the resultant product often has a thin coating of silicone rubber over the exterior of the electrode coil, reducing or eliminating its ability to function as an electrode. The present invention is directed toward solving this problem, and employs a plasma etching step which serves both to remove silicone from the exposed periphery of the electrode coil and to etch away some of the silicone rubber in between the coils so that they stand out from the lead body, displaying a corrugated surface.

BRIEF DESCRIPTION OF THE DRAWINGS

FIG. 1 is a side, plan view of an epicardial defibrillation lead having an electrode which may be manufactured using the method of the present invention.

FIG. 1 is a side, cutaway view through a portion of the electrode on the lead illustrated on FIG. 1, prior to the plasma etching process.

FIG. 3 is a side, cutaway view through the same portion of the electrode illustrated in FIG. 2, after the plasma etching process.

DETAILED DESCRIPTION OF THE INVENTION

FIG. 1 shows a side, plan view of a defibrillation lead 12. At the proximal end of lead 10 is a connector assembly 14 which includes a conductive stepped diameter connector pin 16, extending from the proximal end. Distal pin 16 is an insulative sleeve 24. Extending distally from the connector assembly 14 is an elongated insulative lead body 28 which contains one or more coiled conductors extending from connector pin 16 to electrode 12. In the embodiment illustrated, lead body 28 is an elongated plastic tube of silicone rubber, polyurethane or other flexible biocompatible material containing a multifilar coil coupled to connector pin 16.

Ar the distal end of lead 10 is the electrode 12, which is a space wound metal coil surrounding lead body 28. Electrode coil 12 is anchored to the lead body 28 at its proximal end by a silicone rubber sleeve 30 and at its distal end by silicone rubber tip 32 which is rounded to facilitate passage of the lead through the vascular system. Electrode coil 12 may be fabricated of platinum, stainless steel, or other biocompatible inert metal of low resistivity. The connection of electrode 12 to lead body 28 along the majority of its length is illustrated in FIGS. 2 and 3 below.

FIG. 2 illustrates a side, sectional view through a portion of lead 10 in the vicinity of electrode 12. This view illustrates the construction of the lead after backfilling between the coils of electrode 12 with silicone rubber 34. The structure illustrated in FIG. 2 is produced by first sliding the electrode 12 over the lead body 28, containing multifilar conductor coil 36. Coil 36 may be electrically connected to electrode 12 using any of a variety of commercially known methods including swaging, crimping or welding. The lead is then placed inside a tube of heat shrinkable plastic slightly larger than the external diameter of electrode 12, and the tube is shrunk down around electrode 12 to insure a snug fit. Silicone rubber is then injected into the spaces between the individual coils of electrode 12, the upper surface of lead body 28 and the surrounding shrink tube (not illustrated). After the silicone 34 has cured, the shrink tube is removed, leaving the structure illustrated.

Using the above described process to produce the structure of FIG. 2 has been found to result in a thin coating of silicone rubber surrounding the exterior of the coils of electrode 12, effectively insulating them from body tissue. In addition, the area of contact between the shrink tubing and the coil is quite narrow, so that even in those coils which are not completely covered with silicone 32, the exposed portion of the coil is quite small. Both of these deficiencies are remedied by the plasma etching step, described in conjunction with FIG. 3.

FIG. 3 shows the same view as FIG. 2, after the plasma etching step. The inventors have employed the following procedure for plasma etching the lead. After curing of the silicone backfill 34 and removal of the heat shrink tubing, the lead is placed into a Branson/IPC Model 4055/2 plasma etcher. Vacuum is drawn down to 0.3 Torr, and an inlet flow of room air is introduced into the reactor to produce a net pressure of 1.0 Torr. The lead is then treated for 20 minutes at 400 watts.

During the plasma treatment, the silicone 32 is etched from the exterior portion of the electrode coil 12 and is etched back, forming recesses between the individual coils of electrode 12. The etching process exposes a substantial area of the coil to the exterior of the lead, providing a helical band of effective electrode surface. The resultant product is believed to be superior to corresponding electrodes which might be produced by abrasive or solvent processes, in that the plasma etching process leaves no residue whatsoever on the electrode coils, and produces no toxic by-products for disposal. Furthermore, the process does not produce scratches or blemishes which negatively effect the cosmetic appearance of the device. Finally, the process is inexpensive and requires little time or energy, and does not effect the properties of the silicone backfill 34.

While the above example illustrates one particular etching process, it is anticipated that other plasma etching processes, employing other gases and other parameter settings may be used to practice the invention. Purified air, as opposed to room air, is also workable. However, the lack of moisture in purified air may alter the etch rate as compared to room air. The specific process parameters will of course have to be optimized for the particular plasma etcher employed.

Similarly, while the above method is discussed in conjunction with an endocardial electrode, it is anticipated that the same method might be useful in conjunction with an epicardial or subcutaneous electrode having the general configuration illustrated in FIG. 1 of U.S. Pat. No. 4,187,634 for a "EPICARDIAL PATCH ELECTRODE" issued to Holleman et al, Apr. 4, 1989. In particular, FIG. 1 of the Holleman patent illustrates an epicardial electrode having an elongated coil electrode mounted around a silicone tube. Application of the method of the present invention to this electrode structure is also believed feasible. As such, the above specification should be considered exemplary, rather than limiting with regard to the following claims.

In conjunction with the above specification, we claim:

1. A method for producing a medical electrode comprising the steps of:
   sliding a space wound metal coil over a tubular insulative substrate:
   backfilling between the individual turns of said coil with an insulative plastic; and
   etching the backfilled plastic from the exterior periphery of said coil by means of a gas plasma.

* * * * *